(12) United States Patent
Iwakura et al.

(10) Patent No.: US 10,383,917 B2
(45) Date of Patent: Aug. 20, 2019

(54) METHOD FOR THE TREATMENT OF AN AUTOIMMUNE DISEASE WITH AN AGENT COMPRISING CTRP3

(71) Applicant: TOKYO UNIVERSITY OF SCIENCE FOUNDATION, Tokyo (JP)

(72) Inventors: Yoichiro Iwakura, Tokyo (JP); Masanori Murayama, Tokyo (JP)

(73) Assignee: TOKYO UNIVERSITY OF SCIENCE FOUNDATION, Tokyo (JP)

( * ) Notice: Subject to any disclaimer, the term of this patent is extended or adjusted under 35 U.S.C. 154(b) by 229 days.

(21) Appl. No.: 15/036,518

(22) PCT Filed: Nov. 14, 2014

(86) PCT No.: PCT/JP2014/080195
§ 371 (c)(1),
(2) Date: May 13, 2016

(87) PCT Pub. No.: WO2015/072544
PCT Pub. Date: May 21, 2015

(65) Prior Publication Data
US 2016/0287669 A1    Oct. 6, 2016

Related U.S. Application Data

(60) Provisional application No. 61/904,540, filed on Nov. 15, 2013.

(51) Int. Cl.
*A61K 38/19* (2006.01)

(52) U.S. Cl.
CPC ................... *A61K 38/191* (2013.01)

(58) Field of Classification Search
None
See application file for complete search history.

(56) References Cited

U.S. PATENT DOCUMENTS

| | | | |
|---|---|---|---|
| 2003/0044842 A1 | 3/2003 | Desnoyers et al. | |
| 2007/0009516 A1* | 1/2007 | Tran ....................... | C07K 14/47 424/144.1 |

FOREIGN PATENT DOCUMENTS

WO    WO-2012/157479 A1    11/2012

OTHER PUBLICATIONS

Steinman et al (Nat Med. Jan. 6, 2012;18(1):59-65).*
Ma (Modern Drug Discovery 2004, 7(6)).*
Blumberg et al (Nat Med.; 18(1): 35-41).*
Chen et al., "698 Cartonectin (CORS-26) Suppresses Both Fibrotic and Inflammatory Responses of Primary Colonic Fibroblasts Isolated from Strictures of Crohn's Disease Patients", Gastroenterology, Elsevier, Amsterdam, NL, vol. 136, No. 5, May 1, 2009, p. A-A110, XP026111040.
Schaffler et al., "Genomic Organization, Chromosomal Localization and Adipocytic Expression of the Murine Gene for CORS-26 (collagenous repeat-containing sequence of 26 kDa protein)", Biochimica et Biophysica ACTA, Gene Structure and Expression, Elsevier, Amsterdam, NL, vol. 1628, No. 1, Jul. 9, 2003, pp. 64-70, XP004437347.
Extended European Search Report in EP Application No. 14861460.5 dated May 2, 2017, 7 pages.
Hofmann et al., C1q/TNF-related Protein-3 (CTRP-3) is Secreted by Visceral Adipose Tissue and Exerts Antiinflammatory and Antifibrotic Effects in Primary Human Colonic Tissue and Inflamm Bowel Dis 17, 2011, pp. 2462-2471.
Search Report in International Application No. PCT/JP2014/080195 dated Feb. 17, 2015, 6 pages.
Written Opinion in International Application No. PCT/JP2014/080195 dated Feb. 17, 2015, 7 pages.
Akahoshi et al., "Rheumatic Shikkan: Byoin Byotai Kenkyu no Approach Chemokine", Modern Physician, 2000, vol. 20, No. 1, pp. 35-38.
Fujikado et al., Identification of Arthritis-related Gene Clusters by Microarray Analysis of Two Independent Mouse Models for Rheumatoid Arthritis, Arthritis Res Ther 8, 2006, R100, 13 pages.
Ghai et al., "C1q and its Growing Family", Immunobiology 212, 2007, pp. 253-266.
Shapiro et al., The Crystal Structure of a Complement-1q Family Protein Suggests an Evolutionary Link to Tumor Necrosis Factor, Curr Biol 8, 1998, pp. 335-338.
Dunkelberger et al., "Complement and its Role in Innate and Adaptive immune Responses", Cell Res 20, 2010, pp. 34-50.
Maeda et al., "Cartducin, a Paralog of Acrp30/Adiponectin, is Induced During Chondrogenic Differentiation and Promotes Proliferation of Chondrogenic Precursors and Chondrocytes", Journal of Cellular Physiology 206, 2006, pp. 537-544.
Kopp et al., "C1q/TNF-Related Protein-3 Represents a Novel and Endogenous Lipopolysaccharide Antagonist of the Adipose Tissue", Endocrinology 151, 2010, pp. 5267-5278.
Weigert et al., "The Adiponectin Paralog CORS-26 has Anti-Inflammatory Properties and is Produced by Human Monocytic Cells", FEBS Letters 579, 2005, pp. 5565-5570.
Hofmann et al., "C1q/TNF-related Protein-3 (CTRP-3) is Secreted by Visceral Adipose Tissue and Exerts Antiinflammatory and Antifibrotic Effects in Primary Human Colonic Fibroblasts", Inflamm Bowel Dis 17, 2011, pp. 2462-2471.
Akahoshi et al., "Chemokine and Rheumatic Disease", Japanese Journal of Clinical Immunology, vol. 20, No. 6, 1997, pp. 486-488.
Matsuoka et al., "Phenotypes and Mechanisms of Multiple Sclerosis in the Japanese Population", Advance in Research of Nervous System, vol. 50, No. 4, 2006, pp. 539-548.
Murayama et al., "CTRP3 Plays an Important Role in the Development of Collagen-Induced Arthritis in Mice", Biochemical and Biophysical Research Communications 443, 2014, pp. 42-48.

* cited by examiner

Primary Examiner — Brian Gangle
Assistant Examiner — Andrea K McCollum
(74) Attorney, Agent, or Firm — Marshall, Gerstein & Borun LLP

(57) ABSTRACT

Provided is an agent for the treatment of an autoimmune disease, the agent comprising C1q/TNF-related protein 3 (CTRP3), and a method for the treatment of an autoimmune disease, the method comprising: administering an agent, which comprises CTRPb3 for the treatment of an autoimmune disease, to a subject in need of a treatment of an autoimmune disease.

2 Claims, 13 Drawing Sheets
Specification includes a Sequence Listing.

SEQUENCE LISTING

<160> NUMBER OF SEQ ID NOS: 12

<210> SEQ ID NO 1
<211> LENGTH: 246
<212> TYPE: PRT
<213> ORGANISM: Homo sapiens

<400> SEQUENCE: 1

```
Met Leu Trp Arg Gln Leu Ile Tyr Trp Gln Leu Leu Ala Leu Phe Phe
1               5                   10                  15

Leu Pro Phe Cys Leu Cys Gln Asp Glu Tyr Met Glu Ser Pro Gln Thr
            20                  25                  30

Gly Gly Leu Pro Pro Asp Cys Ser Lys Cys Cys His Gly Asp Tyr Ser
        35                  40                  45

Phe Arg Gly Tyr Gln Gly Pro Pro Gly Pro Pro Gly Pro Pro Gly Ile
    50                  55                  60

Pro Gly Asn His Gly Asn Asn Gly Asn Asn Gly Ala Thr Gly His Glu
65                  70                  75                  80

Gly Ala Lys Gly Glu Lys Gly Asp Lys Gly Asp Leu Gly Pro Arg Gly
                85                  90                  95

Glu Arg Gly Gln His Gly Pro Lys Gly Glu Lys Gly Tyr Pro Gly Ile
            100                 105                 110

Pro Pro Glu Leu Gln Ile Ala Phe Met Ala Ser Leu Ala Thr His Phe
        115                 120                 125

Ser Asn Gln Asn Ser Gly Ile Ile Phe Ser Ser Val Glu Thr Asn Ile
    130                 135                 140

Gly Asn Phe Phe Asp Val Met Thr Gly Arg Phe Gly Ala Pro Val Ser
145                 150                 155                 160

Gly Val Tyr Phe Phe Thr Phe Ser Met Met Lys His Glu Asp Val Glu
                165                 170                 175

Glu Val Tyr Val Tyr Leu Met His Asn Gly Asn Thr Val Phe Ser Met
            180                 185                 190

Tyr Ser Tyr Glu Met Lys Gly Lys Ser Asp Thr Ser Ser Asn His Ala
        195                 200                 205

Val Leu Lys Leu Ala Lys Gly Asp Glu Val Trp Leu Arg Met Gly Asn
    210                 215                 220

Gly Ala Leu His Gly Asp His Gln Arg Phe Ser Thr Phe Ala Gly Phe
225                 230                 235                 240

Leu Leu Phe Glu Thr Lys
                245
```

<210> SEQ ID NO 2
<211> LENGTH: 741
<212> TYPE: DNA
<213> ORGANISM: Homo sapiens

<400> SEQUENCE: 2

```
atgctttgga ggcagctcat ctattggcaa ctgctggctt tgttttttcct cccttttttgc    60
ctgtgtcaag atgaatacat ggagtctcca caaaccggag gactacccccc agactgcagt   120
aagtgttgtc atggagacta cagctttcga ggctaccaag gccccccctgg gccaccgggc   180
cctcctggca ttccaggaaa ccatggaaac aatggcaaca atggagccac tggtcatgaa   240
ggagccaaag gtgagaaggg cgacaaaggt gacctggggc ctcgagggga gcggggcag    300
catggcccca aggagagaa gggctacccg gggattccac cagaacttca gattgcattc    360
atggcttctc tggcaaccca cttcagcaat cagaacagtg ggattatctt cagcagtgtt   420
gagaccaaca ttggaaactt ctttgatgtc atgactggta gatttgggggc cccagtatca   480
ggtgtgtatt tcttcacctt cagcatgatg aagcatgagg atgttgagga agtgtatgtg   540
taccttatgc acaatggcaa cacagtcttc agcatgtaca gctatgaaat gaagggcaaa   600
tcagatacat ccagcaatca tgctgtgctg aagctagcca aaggggatga ggtttggctg   660
cgaatgggca tggcgctct ccatggggac caccaacgct tctccacctt tgcaggattc    720
ctgctctttg aaactaagta a                                              741
```

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3

```
gcagtaacaa tggcaacagc ag                                              22
```

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4

```
gctcggtacc catcaagctt at                                              22
```

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5

```
tgaagaaagg gcttgggcat cttt                                            24
```

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6

-continued

```
aagaaacctg ctcccagctc caa                                    23
```

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7

```
gatatgaagg atgttgaagt cggg                                   24
```

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8

```
tctatgcaaa tgcatccttt gagg                                   24
```

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9

```
atgcagagca atatcacaca g                                      21
```

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10

```
gttgattctt gcatctcacc tg                                     22
```

<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11

```
gctcggtacc catcaagctt at                                     22
```

<210> SEQ ID NO 12
<211> LENGTH: 21
<212> TYPE: PRT
<213> ORGANISM: Artificial Sequence
<220> FEATURE:
<223> OTHER INFORMATION: Immunogen

<400> SEQUENCE: 12

Met Glu Val Gly Trp Tyr Arg Ser Pro Phe Ser Arg Val Val His Leu
1               5                   10                  15

Tyr Arg Asn Gly Lys
            20

METHOD FOR THE TREATMENT OF AN AUTOIMMUNE DISEASE WITH AN AGENT COMPRISING CTRP3

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: ASCII (text) file named "50709_SeqListing.txt," 5,436 bytes, created May 12, 2016.

TECHNICAL FIELD

The present invention relates to an agent for the treatment of an autoimmune disease, comprising C1q/TNF-related protein 3 (CTRP3).

BACKGROUND ART

Rheumatoid arthritis (RA) is an autoimmune disease which characteristically causes local inflammation in joints, deformation of joints, and bone destruction. Since inflammatory cytokines such as IL-1, IL-6, TNF-$\alpha$, and IL-17 play significant roles in development of RA, antibodies and inhibitors against these cytokines are used for treatment of RA. Since high-titer autoantibodies are detected in sera of RA patients, antibodies against B cells are also useful for treatment of RA. These approaches have largely improved the effectiveness of RA treatment. However, since there are also patients for whom these treatments are not effective or become ineffective during the treatment, development of a novel therapeutic method has still been demanded.

The inventors previously generated two RA models; one is human T-cell leukemia virus type I (HTLV-I) transgenic (Tg) mice and the other is IL-1 receptor antagonist (IL-1Ra) deficient (KO) mice, both of which spontaneously develop autoimmune arthritis. Because multiple genes are implicated in the development of autoimmune diseases, the inventors searched for novel disease-related genes using DNA microarray techniques. As a result of comprehensive gene expression analysis between RA models and wild-type (WT) mice, the inventors identified 554 genes of which expression changed more than 3 times in both RA models compared with WT mice (N. Fujikado et al., Arthritis Res Ther 8 (2006) R100). The C1qtnf3 gene, which encodes CTRP3 (also named CORS-26, cartducin and cartnectin), is one of such genes and is highly expressed in both models.

CTRP3 is a soluble secreted protein consisted of a short N-terminal variable region, collagen domain and C-terminal complement C1q domain (R. Ghai et al., Immunobiology 212 (2007) pp. 253-266.). CTRP3 belongs to a member of C1q/TNF-related protein (CTRP) family (L. Shapiro et al., Curr Biol 8 (1998) pp. 335-338.), having a crystal structure resembling that of TNF and complement C1q (J. R. Dunkelberger et al, Cell Res 20 (2010) pp. 34-50). Previous reports showed that C1q domain of complement C1q is important for the recognition of antigen-bound IgM or IgG and binding to C1q receptor (C1qR) and also, C1q domain of adiponectin is important for the binding to adiponectin receptors (adipoR1 and adipoR2). CTRP family members are involved in host defense, inflammation and glucose metabolism (R. Ghai et al., Immunobiology 212 (2007) pp. 253-266.). CTRP3 is identified as a growth factor, and promotes proliferation of chondrogenic precursors and chondrocytes (T. Maeda et al., J Cell Physiol 206 (2006) pp. 537-544). Recently, it was reported that CTRP3 reduces an inflammatory cytokine secretion from human adipocytes, monocytes and fibroblasts in vitro (A. Kopp et al., Endocrinology 151 (2010) pp. 5267-5278, J. Weigert et al., FEBS Lett 579 (2005) pp. 5565-5570, C. Hofmann et al., Inflamm Bowel Dis 17 (2011) pp. 2462-2471).

SUMMARY OF INVENTION

Technical Problem

However, physiological roles of CTRP3 in vivo have not been elucidated to date. Roles of CTRP3 in autoimmune diseases such as RA have been understandably unclear. An object of the invention is to provide a novel agent for the treatment of an autoimmune disease.

The inventors prepared knockout mice for C1qtnf3, which is the gene encoding CTRP3 (C1qtnf3$^{-/-}$ mice), and studied the influence of CTRP3 on development of autoimmune arthritis. In addition, the inventors administered CTRP3 to disease model animals, and investigated the effect of CTRP3.

Solution to Problem

The invention includes the following embodiments.

<1> An agent for the treatment of an autoimmune disease, the agent comprising CTRP3.

<2> The agent for the treatment of an autoimmune disease of <1>, wherein the autoimmune disease is rheumatoid arthritis or multiple sclerosis.

<3> A method for the treatment of an autoimmune disease, the method comprising: administering an agent for the treatment of an autoimmune disease, which comprises CTRP3, to a subject in need of a treatment of the autoimmune disease.

<4> The method for the treatment of an autoimmune disease of <3>, wherein the autoimmune disease is rheumatoid arthritis or multiple sclerosis.

<5> A use of CTRP3 as the agent, for the treatment of an autoimmune disease, of <1> or <2>.

<6> A use of CTRP3 in manufacturing the agent, for the treatment of an autoimmune disease, of <1> or <2>.

<7> An animal model of rheumatoid arthritis or multiple sclerosis that is characterized by being deficient in C1qtnf3 gene.

Advantageous Effects of Invention

By the invention, a novel agent for the treatment of an autoimmune disease, a novel method for treating an autoimmune disease, a novel model animal for an autoimmune disease, and the like can be provided.

BRIEF DESCRIPTION OF DRAWINGS

(FIG. 1A) The expression of C1qtnf3 mRNA in the ankle joints of WT mice (WT), HTLV-I Tg mice (Tg), and IL-1 Ra KO mice (KO) were determined by quantitative RT-PCR. (WT:n=6, HTLV-I Tg:n=6, and IL-1 Ra KO:n=7). Average and standard error of the mean (s.e.m.) are shown. *P <0.01, **P <0.001.

(FIG. 1B) Structure of mouse C1qtnf3 locus (WT allele), the C1qtnf3 targeting construct (Targeting vector), and the predicted mutated C1qtnf3 gene (MT allele). Exons are represented by black boxes. For negative selection, a diphtheria toxin gene (DT) was attached to the 5' end of the genomic fragment. SacII (S) was used for linearization.

(FIG. 1C) The homologous recombination of the C1qtnf3 ocus was examined in the EcoRl (E)- or Hindlll (H)-digested genome by Southern blot hybridization using the 5' probe (upper) or 3' probe (lower), respectively.

(FIG. 1D) The lack of C1qtnf3 transcripts was confirmed by RT-PCR, using the primers in the figure (->-<-).

(FIG. 2A) shows incidence of CIA and (FIG. 2B) shows severity score of CIA. These data were combined from two independent experiments (WT: n=16 and C1qtnf3$^{-/-}$n=17).

(FIG. 2C) shows histopathology of the ankle joints at day 42 after IIC/CFA immunization. One of representative histologies is shown in (C). H&E staining. Tibia, talus and navicular bone are represented as Tib, Tal, and Nav, respectively. Scale bars: 300 μm (left), 100 μm (middle), and 30 μm (right).

(FIG. 2D) shows histological score (WT, C1qtrif3$^{-/-}$:n=5 each)). *P <0.05, ***P <0.001. Average and SEM are shown.

(FIGS. 3A, 3B) Complement C3a (A) and C5a (B) levels in plasma at day 7 after IIC/CFA-immunization were measured by ELISA (WT, C1qtrif3$^{-/-}$:n=6 each). "Day 7 after IIC/CFA-immunization" indicates 7th day after a first injection of IIC, wherein the first injection of IIC is conducted on day 0.

(FIG. 3C) The complement activation of the classical pathway (CP), lectin pathway (LP) and alternative pathway (AP) was determined by C3b deposition (WT, C1qtrif3$^{-/-}$: n=8 each). The data were reproduced in another independent experiment with similar results. Average and SEM are shown.

(FIG. 3D) Messenger RNA expression in the ankle joints at day 42 after IIC/CFA-immunization was measured by semi-quantitative PCR (WT, C1qtrif3$^{-/-}$:n=9 each).

(FIG. 3E) IL-6 production from synoviocytes after IL-1α (0-10 pg/ml) stimulation in the absence or presence of 1 ng/ml CTRP3 was measured by ELISA (WT, C1qtrif3$^{-/-}$: n =3 each). All data were reproduced in another independent experiment with similar result. *P <0.05, **P <0.01. Average and SEM are shown.

(FIGS. 4A, 4B) At day 42 after IIC/CFA immunization, the number (A) and cell population (B) in inguinal LNs were analyzed using CD4-, B220- and CD11c-specific antibodies by flow cytometry (WT:n=9, C1qtrif3$^{-/-}$:n=11). Similar results were obtained in another independent experiment.

(FIGS. 4C, 4D) 7th day after IIC/CFA immunization, inguinal LN cells were removed and cultures with IIC (0, 100, 200 μg/ml). Then, IIC-specific proliferative response was measured by [$^3$H]TdR incorporation (C). IFN-γ concentration in the culture supernatant was determined (WT, C1qtrif3$^{-/-}$:n=4 each) (D). Similar results were obtained in another independent experiment.

(FIG. 4E) At day 42 after IIC/CFA immunization, the sera were collected and IIC-specific IgG levels were determined by ELISA. The data from two independent experiments are combined and shown (WT:n=16 and C1qtrif3$^{-/-}$:n=17).

(FIG. 4F) B cells were incubated with anti-IgM Ab (0-10 pg/ml) and CTRP3 (0, 10, 100 ng/ml). Then, the proliferative response was measured by [3H]TdR incorporation (WT, C1qtrif3$^{-/-}$:n=3 each).

(FIG. 4G) IL-1β production from neutrophils after C5a stimulation (0-1 ng/ml) in the presence of CTRP3 0-500 ng/ml) was measured by ELISA (WT, C1qtrif3$^{-/-}$:n=3 each). All data were reproducible in another independent experiment. *P <0.05, **P <0.01. Average and SEM are shown.

(FIG. 5A) shows the incidence of EAE, and (FIG. 5B) shows the severity. These data were obtained by combination of two independent experiments (wild type, n=18; C1qtnf3$^{-/-}$, n=18).

(FIG. 6A) shows the incidence of arthritis, and (FIG. 6B) shows the severity.

DESCRIPTION OF EMBODIMENTS

Figure 1A:
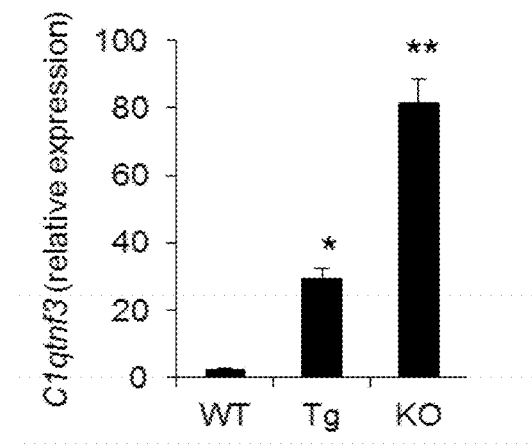
FIGS. 1A-1D explain C1qtnf3$^{-/-}$ mice.
Figure 1B:
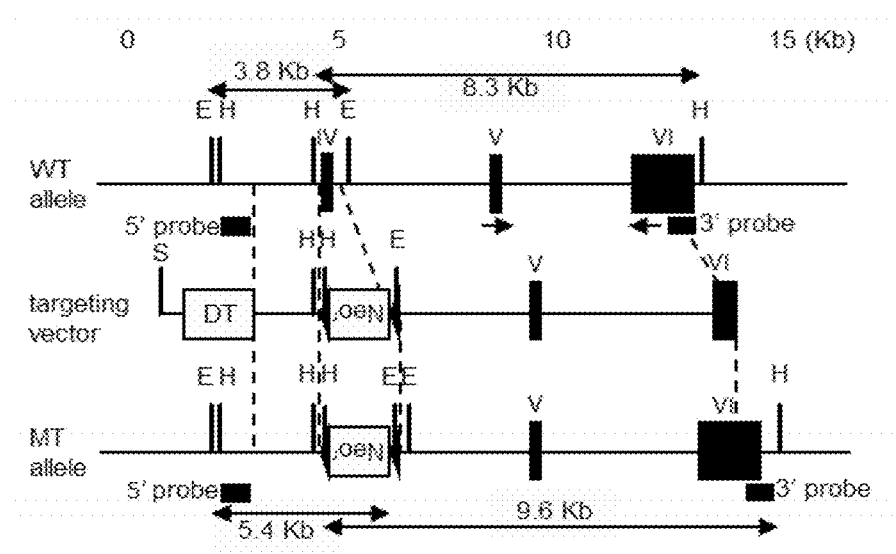

Since CTRP3 receptors and cells expressing the receptors have not yet been identified, accurate elucidation of roles of CTRP3 has been difficult. Despite such a situation, the inventors prepared C1qtnf3$^{-/-}$ mice, and studied the effect of CTRP3 on development of autoimmune arthritis. The inventors administered CTRP3 to model animals of autoimmune arthritis, and, as a result, discovered that the incidence and the severity of autoimmune arthritis can be reduced by the administration. Thus, it was clearly shown that the incidence and the severity of autoimmune arthritis can be reduced by CTRP3. The results indicate that CTRP3 is useful as a pharmaceutical having a novel mechanism of action for treatment of autoimmune diseases such as rheumatoid arthritis (RA).

In the present description, the term "step" includes not only an independent step, but also a step which cannot be clearly distinguished from another step, as long as an expected purpose of the step can be achieved therewith.

In the description, a numerical range indicated using "to" means the range in which the values described before and after "to" are included as the minimum value and the maximum value, respectively.

In the description, the amount of each component in a composition means, in cases where plural substances corresponding to the component are present in the composition, the total amount of the plural substances present in the composition, unless otherwise specified.

Embodiments of the invention are described below.

An autoimmune disease is a disease in which the autoimmune system attacks cells/tissues of the self to cause inflammation and damages of the cells/tissues. Examples of autoimmune diseases include rheumatoid arthritis; multiple sclerosis; systemic lupus erythematosus (lupus); inflammatory intestinal diseases such as Crohn's disease and inflammatory bowel disease; and Behcet disease. The autoimmune disease to which the agent for the treatment of an autoimmune disease or the therapeutic method for an autoimmune disease according to the invention is applied is particularly preferably rheumatoid arthritis or multiple sclerosis.

Rheumatoid arthritis is an autoimmune disease, and causes tissue disorders mediated by cytokines, chemokines, metalloproteases, and the like. In rheumatoid arthritis, inflammation of joints occurs, often leading to progressive destruction of joint structures.

Multiple sclerosis (MS) is an autoimmune disease in which inflammation occurs in the brain, spinal cord, optic nerves, and the like, causing repeated exacerbation of neurological symptoms such as motor paralysis and sensory disturbances, and which targets central nervous myelin sheath antigens. Effectiveness of rituximab for treatment of MS has been reported, and it has been thought that B cells are involved in the pathology of MS.

In terms of CTRP3, human CTRP3 has 246 amino acid residues, and typical amino acid sequences and nucleic acid sequences of human CTRP3 are as described below. Accession Nos. AAI12926, Q9BXJ4, and the like as amino acid sequences of human CTRP3, and Accession Nos. BC112925, EU399231, EU399232, and the like as nucleic acid sequences encoding human CTRP3, are registered in NCBI Genebank. CTRP3 derived from organisms other than human may be used. Amino acid sequences and gene sequences of CTRP3 of organisms other than human are also available from databases such as the Genebank database; published papers; and the like.

```
<Amino acid sequence of human CTRP3
                                    (SEQ ID NO: 1)>
M L W R Q L I Y W Q L L A L F F L P F C L

C Q D E Y M E S P Q T G G L P P D C S K C

C H G D Y S F R G Y Q G P P G P P G P P G

I P G N H G N N G N N G A T G H E G A K G

E K G D K G D L G P R G E R G Q H G P K G

E K G Y P G I P P E L Q I A F M A S L A T

H F S N Q N S G I I F S S V E T N I G N F

F D V M T G R F G A P V S G V Y F F T F S

M M K H E D V E E V Y V Y L M H N G N T V

F S M Y S Y E M K G K S D T S S N H A V L

K L A K G D E V W L R M G N G A L H G D H

Q R F S T F A G F L L F E T K

<Nucleic acid sequence of human CTRP3
                                    (SEQ ID NO: 2)>
A T G C T T T G G A G G C A G C T C A T C

T A T T G G C A A C T G C T G G C T T T G

T T T T T C C T C C C T T T T T G C C T G

T G T C A A G A T G A A T A C A T G G A G

T C T C C A C A A A C C G G A G G A C T A

C C C C C A G A C T G C A G T A A G T G T

T G T C A T G G A G A C T A C A G C T T T

C G A G G C T A C C A A G G C C C C C C T

G G G C C A C C G G G C C C T C C T G G C

A T T C C A G G A A A C C A T G G A A A C

A A T G G C A A C A A T G G A G C C A C T

G G T C A T G A A G G A G C C A A A G G T

G A G A A G G G C G A C A A A G G T G A C

C T G G G G C C T C G A G G G G A G C G G

G G G C A G C A T G G C C C C A A A G G A

G A G A A G G G C T A C C C G G G G A T T

C C A C C A G A A C T T C A G A T T G C A

T T C A T G G C T T C T C T G G C A A C C

C A C T T C A G C A A T C A G A A C A G T

G G G A T T A T C T T C A G C A G T G T T

G A G A C C A A C A T T G G A A A C T T C

T T T G A T G T C A T G A C T G G T A G A

T T T G G G G C C C C A G T A T C A G G T

G T G T A T T T C T T C A C C T T C A G C

A T G A T G A A G C A T G A G G A T G T T

G A G G A A G T G T A T G T G T A C C T T

A T G C A C A A T G G C A A C A C A G T C

T T C A G C A T G T A C A G C T A T G A A

A T G A A G G G C A A A T C A G A T A C A

T C C A G C A A T C A T G C T G T G C T G

A A G C T A G C C A A A G G G G A T G A G

G T T T G G C T G C G A A T G G G C A A T

G G C G C T C T C C A T G G G G A C C A C

C A A C G C T T C T C C A C C T T T G C A

G G A T T C C T G C T C T T T G A A A C T

A A G T A A
```

An embodiment of the invention is an agent for the treatment of an autoimmune disease, containing CTRP3. The method of production of the CTRP3 is not limited, and the CTRP3 may be obtained by a genetic recombination method, synthetic method, or the like based on a known amino acid sequence or polynucleotide sequence. Alternatively, a commercially available product may be used.

In cases where the CTRP3 is produced by a genetic recombination method, a gene encoding CTRP3 may be introduced into a microorganism such as *E. coli* or yeast, plant cell, insect cell, or animal cell, using an expression vector, and the microorganism or cell may be allowed to express CTRP3. In cases where human CTRP3 is to be produced, mammalian cells are particularly preferably used from the viewpoint of maintenance of a stereostructure and post-translational modification. The production of CTRP3 by a chemical synthesis method may be carried out by a liquid phase method, solid phase method, Boc method, Fmoc method, and/or the like which may be carried out singly, or in combination of two or more thereof. Examples of the commercially available product include recombinant human CTRP3 (Aviscera Bioscience, Inc., USA).

The CTRP3 may be a mutant CTRP3 having an amino acid sequence which is the same as a known amino acid sequence except that an amino acid residue(s) is/are partially added, substituted, and/or deleted, or may be a mutant CTRP3 having a polynucleotide sequence which is the same as a known polynucleotide sequence except that one or more bases are added, substituted, and/or deleted, as long as the physiological function of the CTRP3 is not deteriorated. The CTRP3 may be a derivative of CTRP3. The derivative of CTRP3 is not limited, and may be selected depending on the purpose, if appropriate. Examples of the derivative of CTRP3 include derivatives prepared by binding a sugar chain, oligonucleotide, polynucleotide, or polyethylene glycol, or another pharmaceutically acceptable additive or treatment agent, to CTRP3.

The method of administration of the agent for the treatment for an autoimmune disease according to the invention is not limited, and may be either parenteral administration or oral administration. In cases where the administration is parenterally carried out by intraarticular injection, intramuscular injection, intravenous injection, or subcutaneous injection, it is preferred to prepare an aseptic solution supplemented with, as a formulation additive, a solute such as salt or glucose as an isotonic agent, and to administer the prepared solution. Examples of pharmaceutical compositions suitable for the parenteral administration include injections, drip infusions, inhalants, transdermal formulations, and transmucosal formulations. The agent for the treatment of an autoimmune disease according to the invention is preferably, but does not necessarily need to be, administered as an injection by intraarticular injection or intravenous injection. Examples of formulations suitable for the injection solution include aqueous injections, nonaqueous injections, suspension injections, emulsion injections, freeze-dried injections, powder injections, filled injections, and cartridge agents.

Examples of formulations suitable for oral administration include tablets, capsules, powders, granules, liquids, and elixirs.

The dose of the agent for the treatment of an autoimmune disease according to the invention may be any dose as long as it is effective as an agent for the treatment of the autoimmune disease. For example, the dose may be from 0.1 µg/kg to 10 mg/kg/day in terms of the dose of CTRP3. The dose is preferably increased or decreased depending on the age, disease state, symptoms, and/or the like, if appropriate. The therapeutic agent may be administered plural times. In cases where the therapeutic agent is administered plural times, the dosing interval is preferably increased or decreased depending on the disease state, symptoms, and/or the like, if appropriate.

The agent for the treatment of an autoimmune disease according to the invention may be administered in combination with one or more other agents. For example, the agent may be combined with a steroid drug, high-molecular-weight hyaluronan, or nonsteroidal anti-inflammatory drug (NSAID) to provide a mixture or a kit.

Examples of formulation additives of the agent for treating an autoimmune disease according to the invention include liquid media such as water, physiological saline, and solutions of dextrose and similar sugars; glycols such as ethylene glycol, propylene glycol, polyethylene glycol, and polypropylene glycol; antioxidants such as sulfites; pH adjusting agents and buffers such as sodium citrate, sodium acetate, and sodium phosphate; stabilizers such as sodium pyrosulfite, EDTA, thioglycolic acid, and thiolactic acid; isotonic agents such as sodium chloride and glucose; local anesthetics such as procaine hydrochloride and lidocaine hydrochloride; and surfactants such as dimethylsulfoxide (DMSO). One or more other known additives may be included as long as the additives are suitable for the formulation.

The animal species to which the agent is to be administered is not limited, and may be selected depending on the purpose, if appropriate. Examples of the animal species include human, monkey, pig, cow, sheep, goat, dog, cat, mouse, rat, guinea pig, rabbit, and birds. The animal species to which the agent is to be administered is preferably, but does not necessarily need to be, the same as the animal species from which the CTRP3 contained in the autoimmune disease is derived. For example, in cases where the subject to which the agent is to be administered is human, it is preferred to use human CTRP3, a mutant CTRP3 derived from human CTRP3, or a derivative thereof from the viewpoint of increasing the effect as a therapeutic agent and reducing side effects such as immune reaction. However, CTRP3 derived from another animal may be used even in cases where the agent for the treatment of an autoimmune disease is to be used for human.

An embodiment of the invention encompasses a method of treating an autoimmune disease, which method includes administration of an agent, which contains CTRP3, to a subject in need of treatment of the autoimmune disease. The animal species to which the agent is to be administered is not limited, and may be selected depending on the purpose, if appropriate. The agent may be administered to human, or to a non-human animal. Examples of the non-human animal include primates such as monkey; mammals such as pig, cow, sheep, goat, dog, cat, mouse, rat, guinea pig, and rabbit; and avian such as birds. The autoimmune disease is preferably rheumatoid arthritis or multiple sclerosis.

An embodiment of the invention encompasses an animal model for an autoimmune disease such as rheumatoid arthritis, characterized in that the animal is a C1qtnf3 gene-deficient animal. The animal model for an autoimmune disease may be either homozygously or heterozygously deficient in the C1qtnf3 gene. The animal mosel is preferably homozygously deficient in the C1qtnf3 gene. The subject animal species is not limited. Mice or rats are preferably used. Since no association between CTRP3 and an autoimmune disease is known, a novel model animal for an autoimmune disease can be provided. The animal is especially suitable as a model animal for rheumatoid arthritis or multiple sclerosis.

A sequence of the C1qtnf3 gene is known as mentioned above. Methods of preparation of model animals deficient in the C1qtnf3 gene are known, and the known methods may be used. Examples of the methods include a method in which C1qtnf3 gene-deficient embryonic stem cells are provided by homologous recombination, and the cells are then injected into mouse blastocysts to prepare chimeric mice, followed by crossing chimeric mice having germ cells deficient in the gene.

EXAMPLES

The invention is described below in detail by way of Examples. However, the invention is not limited to the Examples.

Unless otherwise specified, each statistical analysis was carried out by two-sided Student's t-test.

Example 1

Preparation of C1qtnf3$^{-/-}$ Mice

The inventors previously identified C1qtnf3 as a candidate for an autoimmune-related gene based on comprehensive gene expression analysis using DNA microarrays of two kinds of RA models, HTLV-I Tg mice and IL-1Ra KO mice. Using the qPCR technique, locally increased expression of C1qtnf3 in joints of the RA model mice (HTLV-I Tg mice and IL-1Ra KO mice) was confirmed (FIG. 1A). Expression of C1qtnf3 is reported to be largely increased in joints of K/B×N mice in addition to HTLV-I Tg mice II and IL-1Ra$^{-/-}$ mice (Reference 22). C1qtnf3$^{-/-}$ mice were prepared to study the influence of CTRP3 on development of CIA.

Figure 1C:
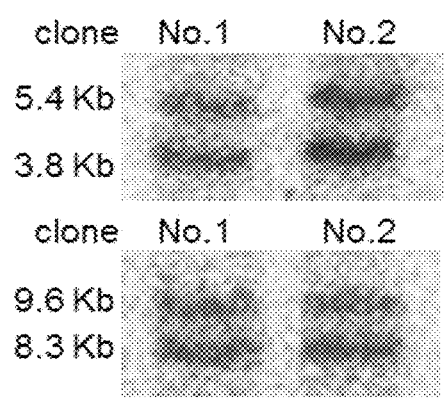

Genomic DNA containing C1qtnf3 gene was isolated from EGR-101 ES cells derived from C57BL/6 embryos (Reference 14). The targeting vector was constructed by replacing a 170 bp genomic fragment containing the exon 4 of the C1qtnf3 gene, which encodes the C1q domain, with the 1.7 Kb DNA fragment containing neomycin resistance gene (Neo$^r$) under the phosphoglycerate kinase (PGK) 1 promoter which was flanked by the lox P sequences. For the negative selection of targeted ES clones, a diphtheria toxin (DT) A gene under the MC1 promoter was ligated to the 3' end of the targeting vector. The targeting vector was electoporated into ES cells and G418-resistant clones were selected (Nacalai Tesque, Japan). Homologous recombinant ES clones were screened by PCR and Southern blotting (FIG. 1C). The following PCR primers were used:

```
                               (Seq ID NO: 3)
    5'-GCAGTAACAATGGCAACAGCAG-3', (Seq ID NO: 4)
    5'-GCTCGGTACCCATCAAGCTTAT-3'.
```

As a 5' probe, a DNA fragment that was amplified using the following primers was used;

```
                               (Seq ID NO: 5)
    5'-TGAAGAAAGGGCTTGGGCATCTTT-3'

(Seq ID NO: 6)
    5'-AAGAAACCTGCTCCCAGCTCCAA-3'.
```

As a 3'probe, DNA fragment that was amplified using the following primers was used;

```
                               (Seq ID NO: 7)
    5'-GATATGAAGGATGTTGAAGTCGGG-3', (Seq ID NO: 8)
    5'-TCTATGCAAATGCATCCTTTGAGG-3'.
```

After karyotype analysis of the targeted ES clones, chimeric mice were generated by an aggregation method (Reference 15). The genotyping of the C1qtnf3 knock-out mice were carried out using the following PCR primers:

```
                               (Seq ID NO: 9)
    primer 1,   5'-GATGCAGAGCAATATCACACAG-3';

(Seq ID NO: 10)
    primer 2,   5'-GTTGATTCTTGCATCTCACCTG-3';

(Seq ID NO: 11)
    primer 3,   5'-GCTCGGTACCCATCAAGCTTAT-3'.
```

Primers 1 and 2 were used for detecting the WT allele (336 bp) and primers 1 and 3 were used for mutant allele (195 bp).

Figure 1D:
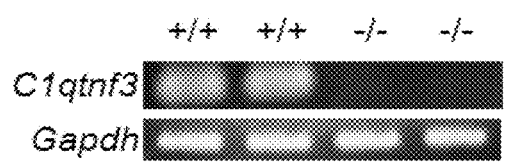

Deficiency of C1qtnf3 transcript was confirmed by RT-PCR (FIG. 1D). The C1qtnf3$^{-/-}$ mice were fertile, and born at the expected mendelian ratio. The mice did not show obvious abnormality before the age of 1 year.

CTRP3 is also implicated in chondrogenesis, because the proliferation of chondrogenic precursor cells and chondrocytes was enhanced by this protein in vitro (References 10 and 23). The involvement in the development of mandibular condylar cartilage is also suggested (Reference 23). However, no obvious skeletal abnormalities in the C1qtnf3$^{-/-}$ mice was detected; they were fertile and were born in the expected Mendelian ratios without any obvious skeletal deformity. There may be possibility that the effects of CTRP3-deficiency are compensated by other CTRP family members, because other CTRP family members, such as adiponectin, are also involved in the regulation of chondrogenesis (Reference 24).

Example 2

Incidence and Severity of Collagen-induced Arthritis (CIA) in C1qtnf3$^{-/-}$ Mice 1. Induction of Collagen-Induced Arthritis (CIA)

In order to evaluate the role of CTRP3 in the development of autoimmune arthritis, CIA was induced using the C1qtnf3$^{-/-}$ mice.

The WT female mice or the C1qtnf3$^{-/-}$ mice were immunized with 100 μl of 2 mg/ml of type II collagen (IIC) (Sigma, USA) emulsified with complete Freund's adjuvant (CFA). CFA contained incomplete Freund's adjuvant (Thermo Scientific, USA) and 1.65 mg/ml of heat-killed *Mycobacterium tuberculosis* (H37Ra; Difco, USA), and was injected intradermally at three sites near the base of the tail on day 0. On day 21, intradermal booster injection of an equal amount of the IIC/CFA was carried out in the vicinities of the previous injection sites.

2. Evaluation of Development of Collagen-Induced Arthritis (CIA) by Clinical Score The development of arthritis was evaluated by macroscopic evaluation. Arthritis development in each paw was graded as follows: 0=no change; 1=mild swelling; 2=obvious joint swelling; 3=severe joint swelling and ankylotic changes (maximum of 12 points for individual mouse) (References 19 and 20). The incidence of CIA was evaluated by chi-square test.

Figure 2A:
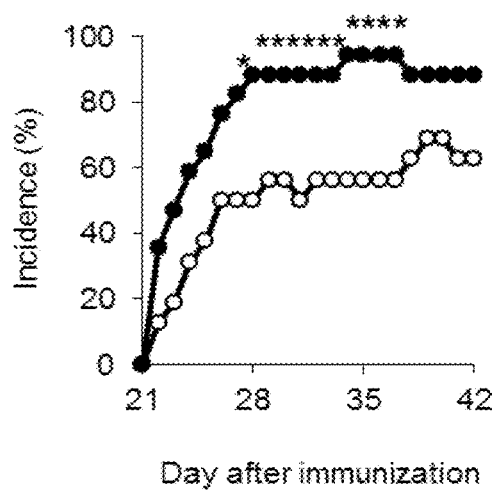
FIGS. 2A-2D show that Collagen-induced arthritis (CIA) is exacerbated in C1qtnf3$^{-/-}$ mice.
Figure 2B:
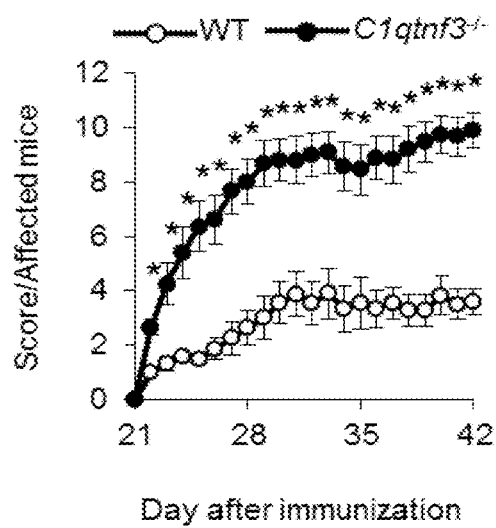

As shown in FIG. 2A, compared to wild-type mice, the incidence of arthritis was higher in the C1qtnf3$^{-/-}$ mice, and the clinical score of arthritis was much higher in the C1qtnf3$^{-/-}$ mice (FIG. 2B). The clinical score was evaluated by Mann-Whitney U test.

3. Evaluation of Development of Collagen-Induced Arthritis (CIA) by Histopathological Diagnosis The mice were sacrificed under ether anesthesia and ankle joints of hind limbs were removed, fixed, decalcified and paraffin embedded for histopathology. Serial sections of 2-3 μm thick were taken sagittally through the talus and stained with H&E for examination by light microscopy. The lesions, including the calcaneus bone and anterior and posterior synovial tissues of the ankle joints, were evaluated histopathologically. Each joint was graded on a scale of 0-3, where 0=normal, 1=thickening and proliferation of the synovial lining, with slight inflammatory cell infiltration, 2=grade 1 changes plus granulomatous lesions in the synovial sublining tissue, and 3=grade 2 changes plus pannus formation and bone destruction. Arthritis index of the ankle joint was estimated from the average grade of talus and around bones including tibia and calcaneum of each mouse (Reference 20).

Figure 2C:
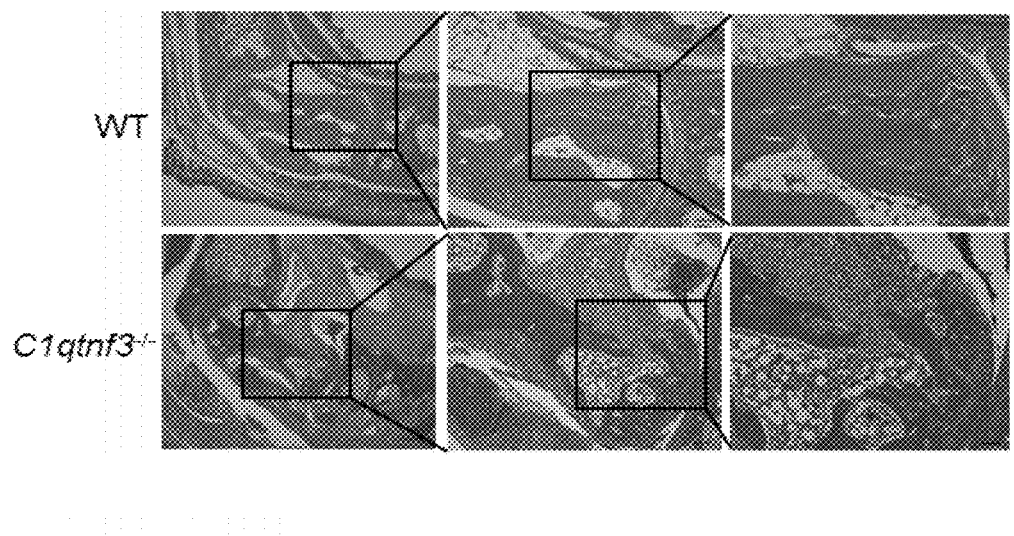
Figure 2D:
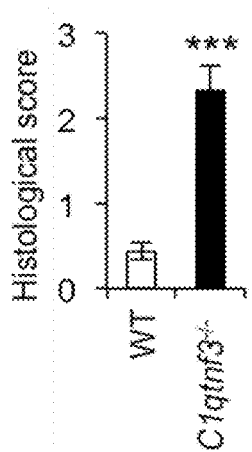

Histological examination of the ankle joints of the WT mice at day 42 after first IIC/CFA-immunization showed mild pathological changes. In contrast, that of the C1qtnf3$^{-/-}$ mice showed much severe changes compared to the WT mice, including proliferation of synovial lining cells, infiltration of inflammatory cells, and bone destruction associated with pannus formation (FIGS. 2C and 2D).

It was shown that severe exacerbation of CIA occurs in the C1qtnf3$^{-/-}$ mice. From these results, it was shown that CTRP3 suppresses development of CIA.

Example 3

Analysis of Roles of CTRP3 in RA

1. Roles in Complement System

Figure 3A:
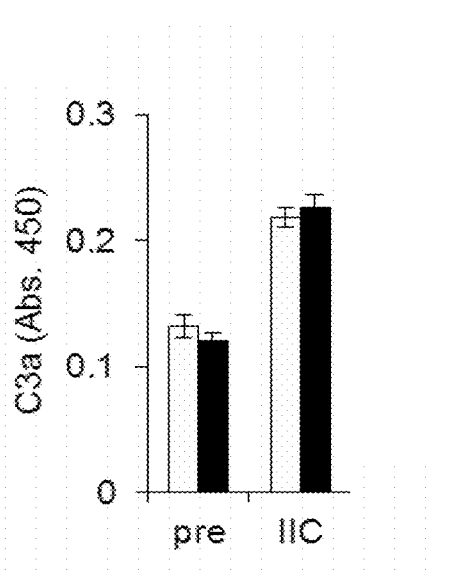
FIGS. 3A-3E show that inflammation is augmented in C1qtnf3$^{-/-}$ mice.
Figure 3B:
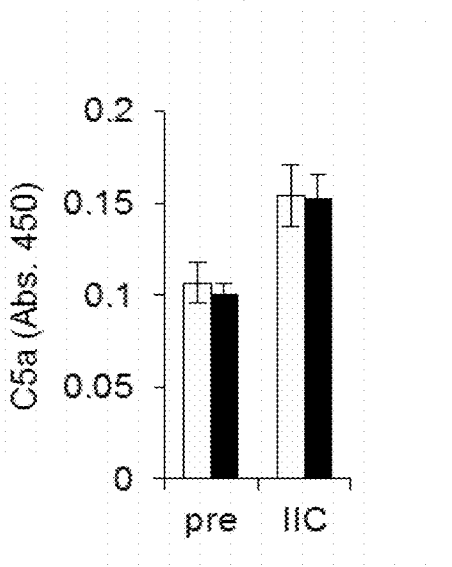
Figure 3C:
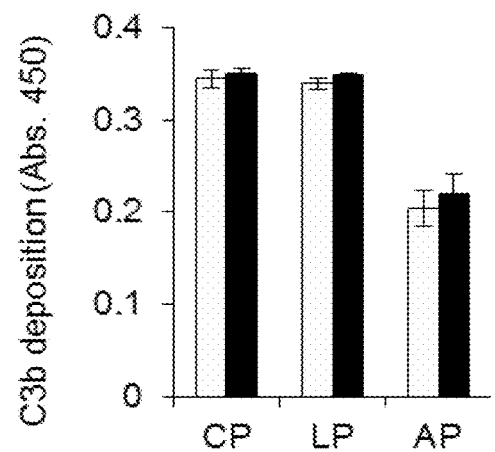

Since CTRP3 has a complement C1q domain, possible involvement of the complement system in the CTRP3 function was studied. Plasma was collected from mice on Day 7 after the first immunization with IIC/CFA, and the levels of complement activation products C3a and C5a were measured by ELISA. The plasma levels of C3a and C5a were measured by sandwich ELISA using a capture antibody-coated plate and a detection antibody against C3a or C5a (BD Pharmingen, USA), using plasma which was derived from female mice (from 8 to 10 weeks old) and chelated with 10 mM EDTA. As a result, it was shown that the C3a and C5a levels in C1qtnf3-/- mice are similar to the C3a and C5a levels in C1qtnf3$^{+/+}$ mice (FIGS. 3A and 3B).

The influence of CTRP3 on complement activation was studied by an in vitro complement activation assay.

Plates (Nunc, Denmark) were coated with OVA/anti-OVA immune complex (OVA: Sigma, USA, and anti-OVA Ab: Millipore, Germany), 50 µg/ml mannans (Sigma, USA), or 200 µg/ml LPS (Sigma, USA) for the assay of complement activation of the classical pathway (CP), lectin pathway (LP) and alternative pathway (AP), respectively (References 16, 17 and 18). Serum was obtained from male mice and was diluted with GVB$^{++}$ buffer for the assay of the CP and LP activity and with GVB/Mg$^{2+}$EGTA buffer for the AP activity. Diluted mouse serum (10%) was incubated on plates at 37° C. for 1 hour and the reaction was stopped by cold 20 mM EDTA/PBS. The deposition of C3b was detected by rat monoclonal antibody against mouse C3 (Abcam, UK). From these results, it was founded that deficiency of CTRP3 does not have influence on complement activation in vitro.

Involvement of CTRP family members in the regulation of the complement system is also suggested, because adiponectin is involved in the regulation of the complement classical pathway by activating C1q (Reference 25) and of the alternative pathway in collaboration with complement factor H (Reference 26). However, no abnormalities of the complement system were detected in the C1qtnf3$^{-/-}$ mice, suggesting that CTRP3 is not involved in the regulation of the complement system. The results of the measurement of C3a and C5a levels and the in vitro complement activation assay show that CTRP3 is not a regulatory factor of complement.

2. Roles in Production of Cytokines

Next, the expression of inflammatory cytokines in the joints at day 42 after first IIC/CFA-immunization were studied in WT mice or C1qtnf3$^{-/-}$ mice.

Figure 3D:
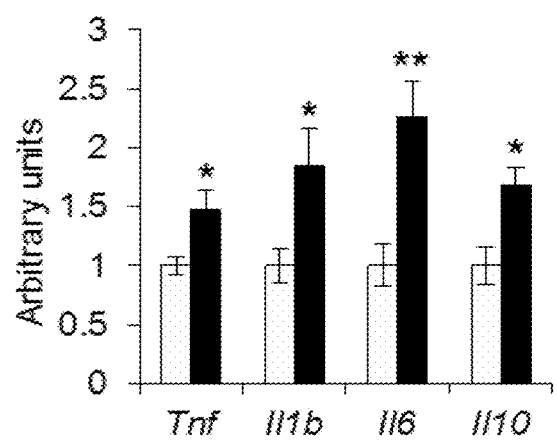

Expression of messenger RNAs of TNF-α, IL-1b, IL-6, and IL-10 in ankle joints was measured by semi-quantitative PCR according to a conventional method. The result showed that cytokine production in the arthritis joints was more enhanced in C1qtnf3$^{-/-}$ mice than that in WT mice (FIG. 3D).

Since these cytokines are known to be released from synoviocytes, whether or not CTRP3 deficiency influences production of inflammatory cytokines from synoviocytes was studied. The primary synoviocytes were harvested from synovium of knee and ankle and were cultured in DMEM medium (Gibco) containing 10% FBS and 1% penicillin-streptomycin. 1×10$^4$ cells were stimulated with IL-1α (0, 1, 5 and 10 pg/ml) for 24 hours in the absence or presence of 1 ng/mL of human recombinant CTRP3 (Adipobioscience, USA) on 96-well plates. Then, IL-6 levels in the culture supernatants after 24 hours were measured with Mouse IL-6 ELISA MAX™ Standard (BioLegend, USA).

Figure 3E:
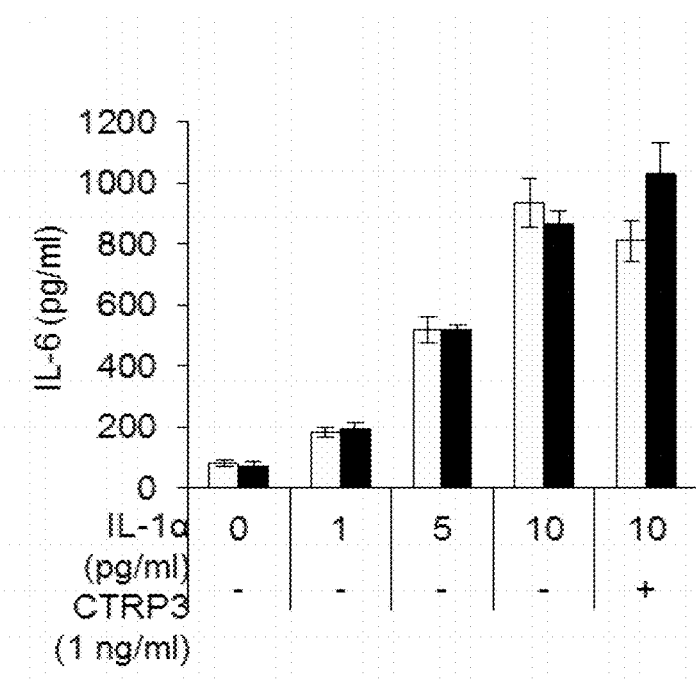

The result showed that IL-6 derived from synoviocytes of C1qtnf3$^{-/-}$ mice is similar to IL-6 derived from synoviocytes of WT mice, and that exogenous CTRP3 does not suppress IL-6 release from synoviocytes (FIG. 3E).

These observations suggest that immune cells infiltrating into the joints, rather than synoviocytes, are responsible for the suppression of inflammation in C1qtnf3$^{-/-}$ mice.

CTRP3 is reported to suppress release of inflammatory cytokines in human monocytes (Reference 12). However, CTRP3 did not suppress production of cytokines in synoviocytes in the joints with arthritis.

3. Roles in Immune Response against IIC

Infiltration of T cells and B cells into the synovial lining and periarticular areas is commonly found in RA patients and RA models. Therefore, the cell composition of lymph node cells collected from regional lymph nodes of WT mice or C1qtnf3–/– mice on Day 42 after the first immunization with IIC/CFA was studied by flow cytometry analysis. Cells were stained with PACIFIC BLUE™ conjugated monoclonal antibodies, FITC-conjugated monoclonal antibodies, and APC-conjugated monoclonal antibodies (mAbs), as previously described (Reference 21). Hamster and rat mAbs against mouse CD3 (145-2C11) and B220 (RA3-6B2) respectively were purchased from Biolegend (USA), and hamster mAb against CD11c (HL3) was purchased from BD Pharmingen (USA). Cells were stained according to standard techniques, and analyzed by a FACS CANTO™ cytometer and either CELLQUEST™ (BectonDickinson, USA) or FLOWJO® software (Tree Star, USA).

Figure 4A:
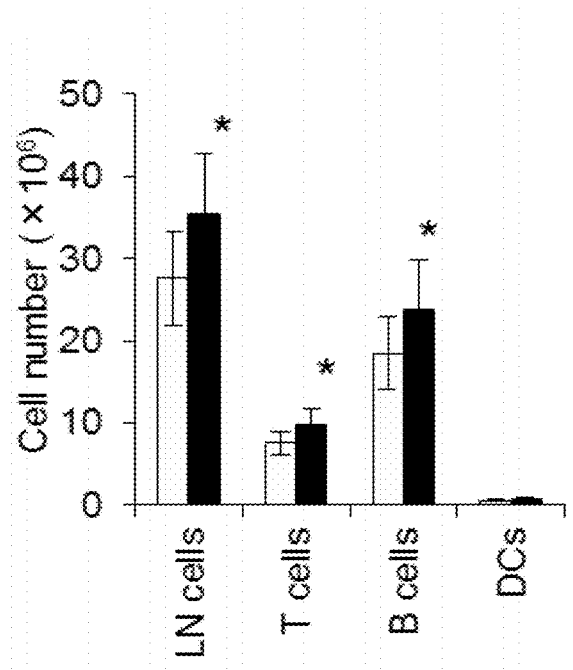
FIGS. 4A-4D show that type II collagen (IIC)-specific antibody production was enhanced in C1qtnf3$^{-/-}$ mice.
Figure 4B:
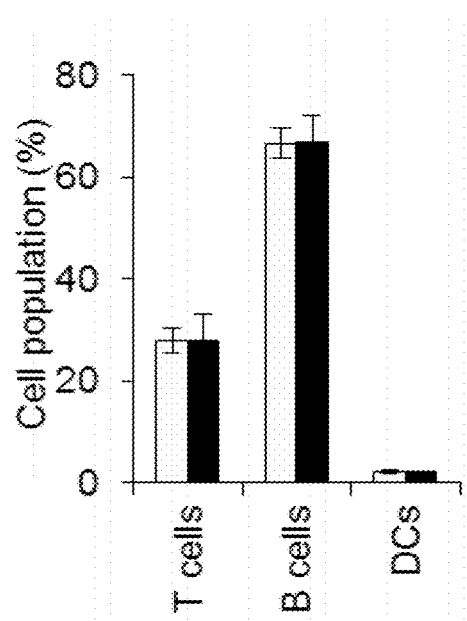

T cell and B cell were increased in lymph node (LN) of C1qtnf3$^{-/-}$ mice than that of WT mice at day 42 after the first IIC/CFA-immunization, but the cell population was comparable between C1qtnf3$^{-/-}$ mice and WT mice (FIGS. 4A and 4B).

Subsequently, llC-specific lymph node (LN) cell proliferative response was studied. LN cells were harvested from a region where arthritis is developed in WT mice or C1qtnf3$^{-/-}$ mice at day 7 after llC-immunization. LN cells were cultured in the absence or presence of 100 µg/mL or 200 pg/mL of denatured llC for 72hours, followed by incorporation of [$^3$H] thymidine (0.25 µCi/ml) (Amersham, U.K.) for 6 hours. Then cells were harvested with Micro 96 cell harvester (Skatron, Norway) and radioactivity was measured with MICRO BETA® (Pharmacia Biotech, USA). IFN-y levels in the culture supernatants from the proliferation assay after 72 hour were measured with Mouse IFN-gamma DUOSET (R&D Systems, USA).

Figure 4C:
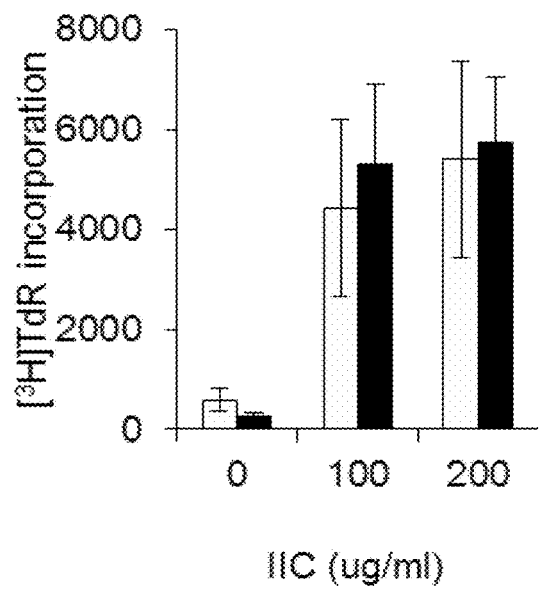
Figure 4D:
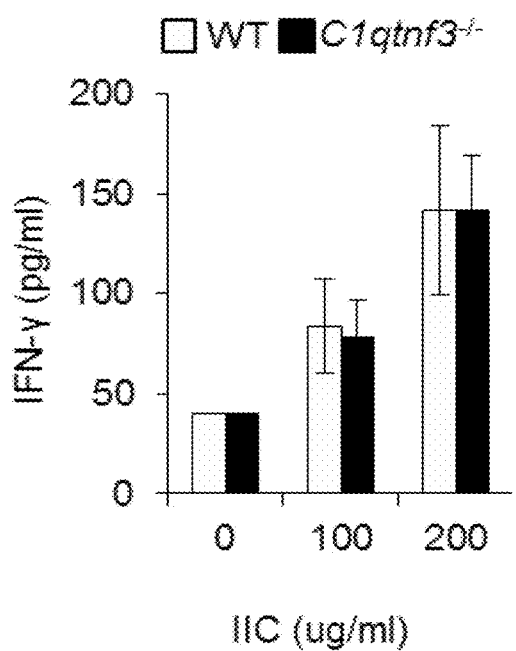

It was found that recall T cell proliferation response was comparable between C1qtnf3$^{-/-}$ mice and WT mice (FIG. 4C). IFN-y production after IIC re-stimulation was also comparable between C1qtnf3$^{-/-}$ and WT LN cell cultures (FIG. 4D). These results suggest that T cell priming in C1qtnf3$^{-/-}$ mice is normal.

Subsequently, IIC-specific IgG production in the C1qtnf3$^{-/-}$ mice was studied. Sera was collected from C1qtnf3$^{-/-}$ mice on day 42 after the first IIC/CFA-immunization, and IIC-specific IgG levels were measured by ELISA. ELIZA was carried out using 20 µg/ml IIC-coated plates and alkaline phosphatase-conjugated polyclonal rabbit antibodies to mouse IgG (Zymed, USA) to measure IIC-specific IgG levels in sera from C1qtnf3$^{-/-}$ mice on day 42 after the first IIC/CFA-immunization.

Figure 4E:
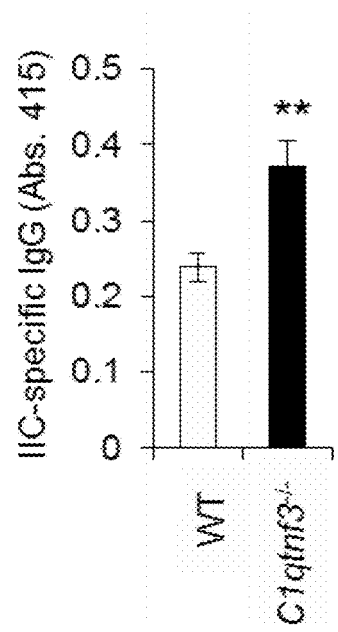
FIGS. 4E-4G show that type II collagen (IIC)-specific antibody production was enhanced in C1qtnf3$^{-/-}$ mice.

The results showed that IIC-specific IgG levels in sera from C1qtnf3$^{-/-}$ mice were significantly higher than that of WT mice (FIG. 4E).

Then, the effect of CTRP3 on B cell proliferation in vitro was examined.

Splenic B cells were purified by anti-mouse B220 microbeads, according to manufactures' instructions (Miltenyi Biotec, Germany). B220$^+$ cells were cultured with anti-mouse IgM F(ab)'$_2$ fragment (0, 1, 5 and 10 µg/ml) (Jackson ImmunoResearch, USA) for 72 hours, followed by incorporation of [$^3$H] thymidine (0.25 µCi/ml) (Amersham, U.K.) for 6 hours. Then, the radioactivity in the harvested cells was measured.

Figure 4F:
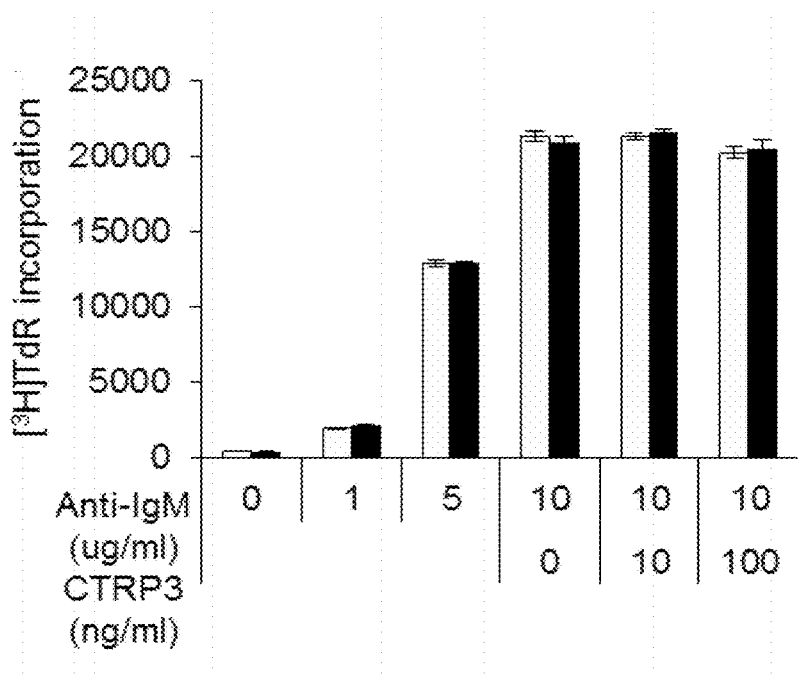

The IIC-specific IgG levels in sera of the C1qtnf3$^{-/-}$ mice were significantly higher than the IIC-specific IgG levels in sera of wild-type mice. It was therefore shown that production of antibodies against IIC remarkably increases in C1qtnf3$^{-/-}$ mice after induction of CIA. However, the B cell proliferation induced by anti-IgM was comparable between C1qtnf3$^{-/-}$ B cells and WT B cells, and exogenous CTRP3 did not suppress B cell proliferation (FIG. 4F).

Since production of antibodies against IIC is important for development of arthritis, it is suggested that C1qtnf3 deficiency may be a cause of development of CIA in C1qtnf3$^{-/-}$ mice. However, since the B cell proliferation response was normal after stimulation with anti-IgM, B cell-intrinsic functions were also normal. No abnormality was detected at all in the recall proliferative response against IIC in T cells of the C1qtnf3$^{-/-}$ mice.

Figure 4G:
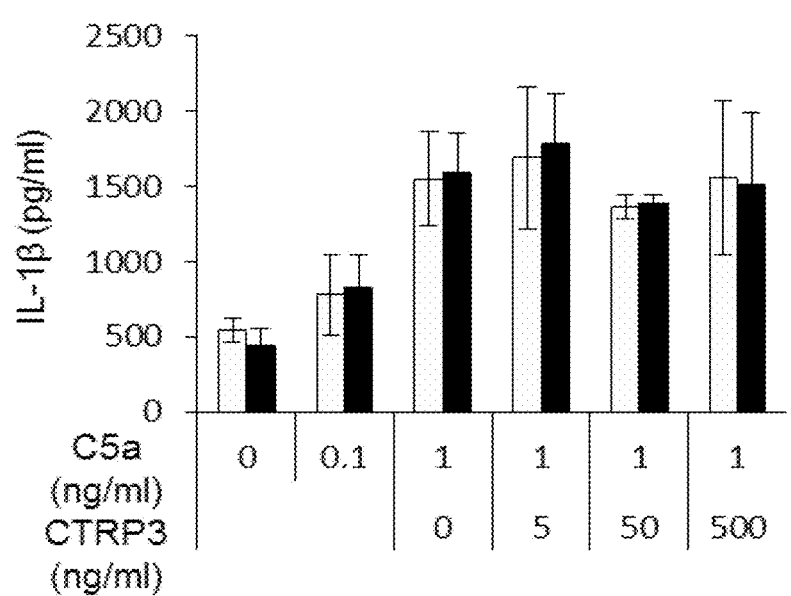

Since C1qtnf3 is expressed in neutrophils, the effect of CTRP3 on activation of neutrophils was studied (FIG. 4G). Neutrophils derived from bone marrow were stimulated by C5a, and IL-1β levels of the culture supernatant were measured. Neutrophils were purified by anti-mouse Ly-6G microbeads (Miltenyi Biotec, Germany). The neutrophils were cultured with C5a (0, 0,1 and 1 µg/ml) (R&D Systems, USA) for 1 hour. Then, IL-1 β levels in the supernatants were measured by Mouse IL-1βELISA MAX™ Standard (Biolegend, USA).

The results showed that IL-1 βproduction from C1qtnf3$^{-/-}$ neutrophils was similar to that of WT mice, and exogenous CTRP3 did not suppress IL-1βrelease from neutrophils (FIG. 4G). Cytokine production after neutrophil activation with complement C5a was normal, suggesting that neutrophils, one of high CTRP3 producers, are not responsible for the elevated inflammation in joints.

These observations suggest that CTRP3 plays an important role in the development of autoimmune arthritis by regulating antibody production. Excessive proliferation of T cells and B cells found in C1qtnf3$^{-/-}$ mice is thought to be responsible for the increased antibody production and exacerbation of arthritis in these mice.

Example 4

Roles of CTRP3 in Multiple Sclerosis

Similarly to rheumatoid arthritis, multiple sclerosis is an autoimmune disease. Therefore, the influence of CTRP3 on multiple sclerosis was evaluated using mice prepared by inducing experimental autoimmune encephalomyelitis (EAE), which are multiple sclerosis-induced model mice.

Female wild-type mice or C1qtnf3-/- mice were immunized with 600 µg of MOG$_{35-55}$ peptide (MEVGWYRSPFSRVVHLYRNGK) (SEQ ID NO: 12) (manufactured by Scrun Japan), which is a part of myelin oligodendrocyte glycoprotein (MOG), after emulsification with complete Freund's adjuvant (CFA). The CFA contained Freund's incomplete adjuvant (Thermo Scientific, USA) and 5 mg/ml heat-sterilized tubercle bacillus (*Mycobacterium tuberculosis*) (H37Ra; Difco, USA), and was intradermally injected at four positions in the vicinities of the limbs on Day 0. On Day 21, intradermal booster injection of an equal amount of the emulsion was carried out in the vicinities of the previous injection sites.

Figure 5A:
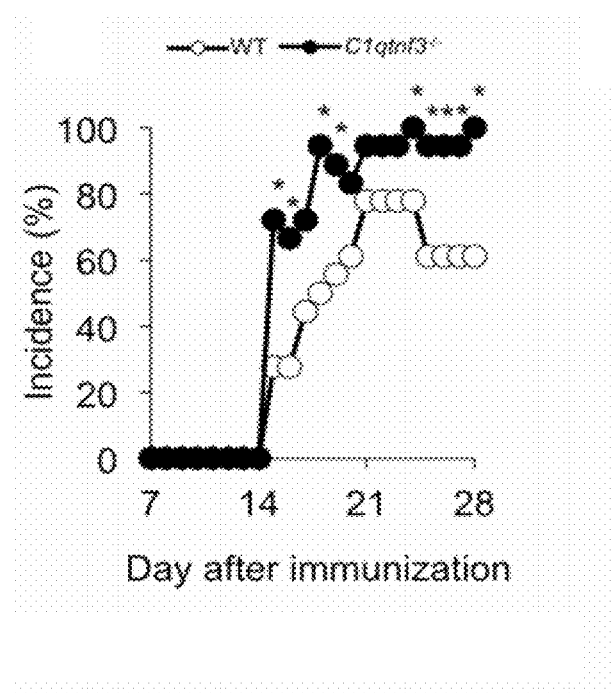
FIGS. 5A and 5B are diagrams showing exacerbation of experimental autoimmune encephalomyelitis (EAE) in C1qtnf3$^{-/-}$ mice.
Figure 5B:
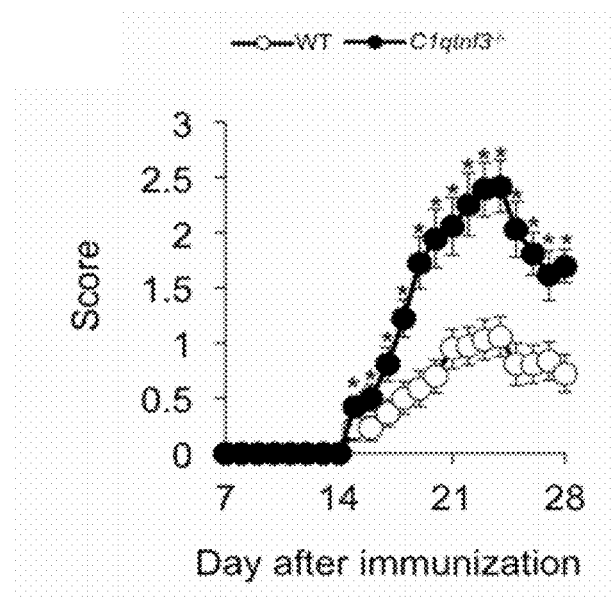

Development of EAE was judged by macroscopic evaluation. The severity was ranked as follows: 0, no change; 0.5, mild paralysis of the tail; 1, paralysis of the tail; 2, mild paralysis of a hindlimb(s); 2.5, paralysis of one of the hindlimbs; 3, paralysis of both hindlimbs; 3.5, paralysis of both hindlimbs and low grip strength of forelimbs; 4, general paralysis. Each mouse was judged as having developed EAE in cases where the rank was not less than 0.5. The incidence of EAE was evaluated by chi-square test (Nature protocols. 2006; 1(4):1810-9). As shown in FIG. 5A, compared to wild-type mice, the C1qtnf3$^{-/-}$ mice showed an increased incidence of EAE, and the C1qtnf3$^{-/-}$ mice showed remarkably increased severity (FIG. 5B). The clinical score was evaluated by Mann-Whitney U test.

From the above results, it was shown that CTRP3 has a suppressive function in development of EAE.

Example 5

Effect of CTRP3 on Arthritis

DBA/1 J mice (female, 6-8 weeks of age, n=6) were immunized with 100 uL of 2 mg/ml chicken type II collagen (IIC/CFA) (Sigma, USA) emulsified with Complete Freund's Adjuvant (Difco, USA) by intradermal injection at three sites near the base of the tail on day 0. On day 21, intradermal booster injection of an equal amount of the IIC/CFA was carried out in the vicinities of the previous injection sites. The mice were daily injected 30 uL of recombinant human CTRP3 (300 ng, Aviscera Bioscience, USA) (SEQ ID NO: 1) into the articular cavity of the left knee joint and PBS as a control into the articular cavity of the right knee joint from day 28.

The development of arthritis in the DBA/1 J mice was evaluated by the following criteria:

Criteria for evaluation of arthritis (Clinical score)

0, no change;

1, erythema and mild swelling confined to the tarsal joints;

2, erythema and mild swelling extending from the tarsal joint to digit;

3, erythema and moderate swelling extending from metatarsal joints;

4, erythema and severe swelling encompassing the ankle, foot, and digits, or ankylosis of the limb.

Figure 6A:
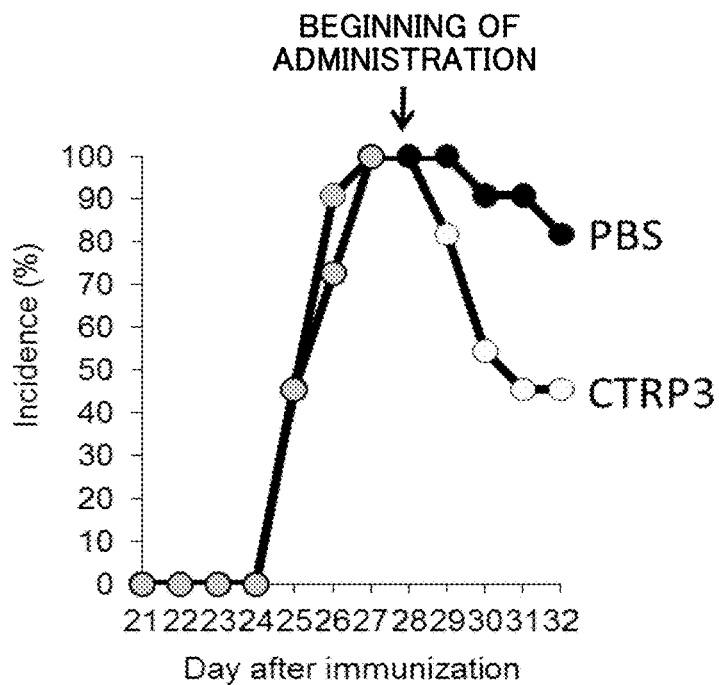
FIGS. 6A and 6B are diagrams showing the therapeutic effect of administration of CTRP3.
Figure 6B:
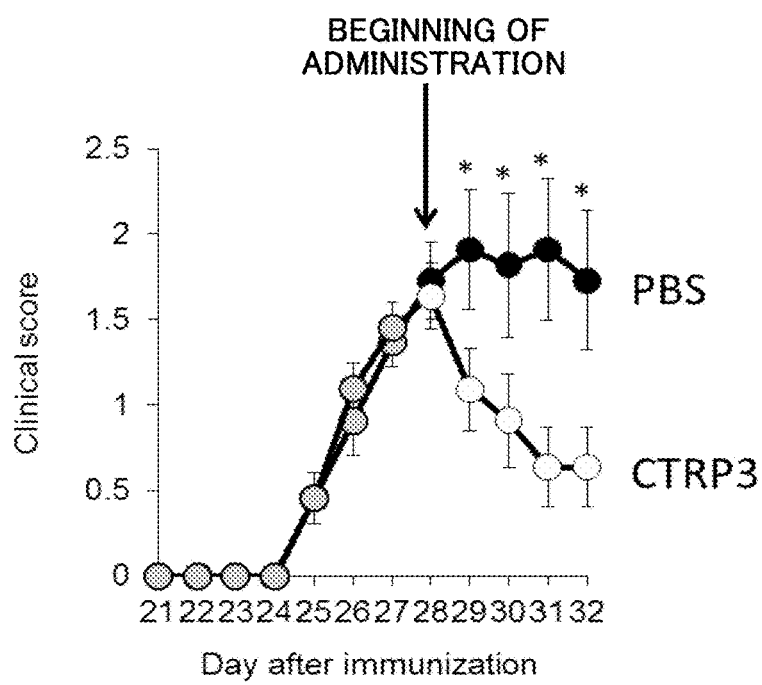

Each mouse was judged as having developed arthritis in cases where the evaluation score for arthritis was not less than 1. The incidence of arthritis is shown in FIG. 6A, and the mean and the standard error of the evaluation score for arthritis are shown in FIG. 6B. The incidence of arthritis was subjected to statistical analysis using chi-square test, and the clinical score was subjected to statistical analysis using Mann-Whitney U test. The administration of CTRP3 reduced the incidence of arthritis, and lowered the clinical score.

It was clearly shown that CTRP3 ameliorates development of autoimmune arthritis. Usefulness of CTRP3 as a pharmaceutical for treatment of autoimmune diseases such as RA was shown.

8-10 week-old C57BL/6 background mice of the same sex were used in all examples except Example 5. Mice were kept under specific pathogen-free conditions in the clean rooms at the Center for Experimental Medicine and Systems Biology, Institute of Medical Science, University of Tokyo and the Research Institute for Biomedical Sciences, Tokyo University of Science. All experiments were approved by the institutional animal use committees and were conducted according to the institutional ethical guidelines for animal experiments and safety guidelines for gene manipulation experiments.

REFERENCES

[1] M. Feldmann, S. R. Maini, Role of cytokines in rheumatoid arthritis: an education in pathophysiology and therapeutics, Immunol Rev 223 (2008) 7-19.

[2] T. Kishimoto, IL-6: from its discovery to clinical applications, Int Immunol 22 (2010) 347-352.

[3] J. C. Edwards, G. Cambridge, Sustained improvement in rheumatoid arthritis following a protocol designed to deplete B lymphocytes, Rheumatology (Oxford) 40 (2001) 205-211.

[4] Y. Iwakura, M. Tosu, E. Yoshida, M. Takiguchi, K. Sato, I. Kitajima, K. Nishioka, K. Yamamoto, T. Takeda, M. Hatanaka, et al., Induction of inflammatory arthropathy resembling rheumatoid arthritis in mice transgenic for HTLV-I, Science 253 (1991) 1026-1028.

[5] R. Horai, S. Saijo, H. Tanioka, S. Nakae, K. Sudo, A. Okahara, T. Ikuse, M. Asano, Y. Iwakura, Development of chronic inflammatory arthropathy resembling rheumatoid arthritis in interleukin 1 receptor antagonist-deficient mice, J Exp Med 191 (2000) 313-320.

[6] N. Fujikado, S. Saijo, Y. Iwakura, Identification of arthritis-related gene clusters by microarray analysis of two independent mouse models for rheumatoid arthritis, Arthritis Res Ther 8 (2006) R100.

[7] R. Ghai, P. Waters, L. T. Roumenina, M. Gadjeva, M. S. Kojouharova, K. B. Reid, R. B. Sim, U. Kishore, C1q and its growing family, Immunobiology 212 (2007) 253-266.

[8] L. Shapiro, P. E. Scherer, The crystal structure of a complement-1q family protein suggests an evolutionary link to tumor necrosis factor, Curr Biol 8 (1998) 335-338.

[9] J. R. Dunkelberger, W. C. Song, Complement and its role in innate and adaptive immune responses, Cell Res 20 (2010) 34-50.

[10] T. Maeda, A. Jikko, M. Abe, T. Yokohama-Tamaki, H. Akiyama, S. Furukawa, M. Takigawa, S. Wakisaka, Cartducin, a paralog of Acrp30/adiponectin, is induced during chondrogenic differentiation and promotes proliferation of chondrogenic precursors and chondrocytes, J Cell Physiol 206 (2006) 537-544.

[11] A. Kopp, M. Bala, C. Buechler, W. Falk, P. Gross, M. Neumeier, J. Scholmerich, A. Schaffler, C1q/TNF-related protein-3 represents a novel and endogenous lipopolysaccharide antagonist of the adipose tissue, Endocrinology 151 (2010) 5267-5278.

[12] J. Weigert, M. Neumeier, A. Schaffler, M. Fleck, J. Scholmerich, C. Schutz, C. Buechler, The adiponectin paralog CORS-26 has anti-inflammatory properties and is produced by human monocytic cells, FEBS Lett 579 (2005) 5565-5570.

[13] C. Hofmann, N. Chen, F. Obermeier, G. Paul, C. Buchler, A. Kopp, W. Falk, A. Schaffler, C1q/TNF-related protein-3 (CTRP-3) is secreted by visceral adipose tissue and exerts antiinflammatory and antifibrotic effects in primary human colonic fibroblasts, Inflamm Bowel Dis 17 (2011) 2462-2471.

[14] Y. Fujihara, K. Kaseda, N. Inoue, M. Ikawa, M. Okabe, Production of mouse pups from germline transmission-failed knockout chimeras, Transgenic Res 22 (2013) 195-200.

[15] R. Horai, M. Asano, K. Sudo, H. Kanuka, M. Suzuki, M. Nishihara, M. Takahashi, Y. Iwakura, Production of mice deficient in genes for interleukin (IL)-1alpha, IL-1beta, IL-1alpha/beta, and IL-1 receptor antagonist shows that IL-1beta is crucial in turpentine-induced fever development and glucocorticoid secretion, J Exp Med 187 (1998) 1463-1475.

[16] P. J. Lachmann, Preparing serum for functional complement assays, J Immunol Methods 352 (2010) 195-197.

[17] M. A. Seelen, A. Roos, J. Wieslander, T. E. Mollnes, A. G. Sjoholm, R. Wurzner, M. Loos, F. Tedesco, R. B. Sim, P. Garred, E. Alexopoulos, M. W. Turner, M. R. Daha, Functional analysis of the classical, alternative, and MBL pathways of the complement system: standardization and validation of a simple ELISA, J Immunol Methods 296 (2005) 187-198.

[18] Y. Kimura, T. Miwa, L. Zhou, W. C. Song, Activator-specific requirement of properdin in the initiation and amplification of the alternative pathway complement, Blood 111 (2008) 732-740.

[19] D. E. Trentham, A. S. Townes, A. H. Kang, Autoimmunity to type II collagen an experimental model of arthritis, J Exp Med 146 (1977) 857-868.

[20] J. J. Inglis, E. Simelyte, F. E. McCann, G. Criado, R. O. Williams, Protocol for the induction of arthritis in C57BL/6 mice, Nat Protoc 3 (2008) 612-618.

[21] N. Fujikado, S. Saijo, T. Yonezawa, K. Shimamori, A. Ishii, S. Sugai, H. Kotaki, K. Sudo, M. Nose, Y. Iwakura, Dcir deficiency causes development of autoimmune diseases in mice due to excess expansion of dendritic cells, Nat Med 14 (2008) 176-180.

[22] S. Garcia, J. Forteza, C. Lopez-Otin, J. J. Gomez-Reino, A. Gonzalez, C. Conde, Matrix metalloproteinase-8 deficiency increases joint inflammation and bone erosion in the K/BxN serum-transfer arthritis model, Arthritis Res Ther 12 (2010) R224.

[23] T. Yokohama-Tamaki, T. Maeda, T. S. Tanaka, S. Shibata, Functional analysis of CTRP3/cartducin in Meckel's cartilage and developing condylar cartilage in the fetal mouse mandible, J Anat 218 (2011) 517-533.

[24] K. M. Tong, C. P. Chen, K. C. Huang, D. C. Shieh, H. C. Cheng, C. Y. Tzeng, K. H. Chen, Y. C. Chiu, C. H. Tang, Adiponectin increases MMP-3 expression in human chondrocytes through AdipoR1 signaling pathway, J Cell Biochem 112 (2011) 1431-1440.

[25] P. W. Peake, Y. Shen, A. Walther, J. A. Charlesworth, Adiponectin binds C1q and activates the classical pathway of complement, Biochem Biophys Res Commun 367 (2008) 560-565.

[26] P. Peake, Y. Shen, Factor H binds to the N-terminus of adiponectin and modulates complement activation, Biochem Biophys Res Commun 397 (2010) 361-366.

The disclosure of U.S. provisional patent application No. 61/904,540, filed on Nov. 15, 2013, is hereby incorporated by reference in its entirety.

All the documents, patent applications, and technical standards described in the present description are hereby incorporated by reference to the same extent as in cases where each document, patent application, or technical standard is concretely and individually described to be incorporated by reference.

The above description on exemplary embodiments according to the invention was done for the purposes of exemplification and explanation, and intends neither to provide comprehensive description nor to limit the invention to the modes disclosed. As is evident, many modifications and changes are obvious to those skilled in the art. The embodiments were selected and described so that the embodiments best explain the principle and practical application of the invention and allow those skilled in the art other than the present inventors to understand the invention together with various embodiments and various modifications suitable for specific uses that can be assumed. The scope of the scope according to the invention is intended to be specified by the claims described below and equivalents thereof.

The invention claimed is:

1. A method for the treatment of an autoimmune disease comprising: administering an agent comprising human C1q/TNF-related protein 3 (CTRP3) to a subject in need of a treatment of the autoimmune disease, wherein the autoimmune disease is rheumatoid arthritis or multiple sclerosis.

2. The method for the treatment of an autoimmune disease of claim 1, wherein the autoimmune disease is rheumatoid arthritis.

* * * * *

UNITED STATES PATENT AND TRADEMARK OFFICE
CERTIFICATE OF CORRECTION

PATENT NO.        : 10,383,917 B2
APPLICATION NO.   : 15/036518
DATED             : August 20, 2019
INVENTOR(S)       : Yoichiro Iwakura et al.

Page 1 of 1

It is certified that error appears in the above-identified patent and that said Letters Patent is hereby corrected as shown below:

At item (57), Abstract: Line 5, "CTRPb3" should be -- CTRP3 --.

Signed and Sealed this
Ninth Day of June, 2020

Andrei Iancu
*Director of the United States Patent and Trademark Office*